(12) United States Patent
Tirtowidjojo et al.

(10) Patent No.: US 9,233,896 B2
(45) Date of Patent: Jan. 12, 2016

(54) PROCESS FOR THE PRODUCTION OF CHLORINATED PROPENES

(75) Inventors: Max M. Tirtowidjojo, Lake Jackson, TX (US); Barry B. Fish, Lake Jackson, TX (US); David S. Laitar, Midland, MI (US)

(73) Assignee: Blue Cube IP LLC, Midland, MI (US)

( * ) Notice: Subject to any disclaimer, the term of this patent is extended or adjusted under 35 U.S.C. 154(b) by 0 days.

(21) Appl. No.: 14/236,292

(22) PCT Filed: Aug. 4, 2012

(86) PCT No.: PCT/US2012/049669
§ 371 (c)(1),
(2), (4) Date: Jan. 30, 2014

(87) PCT Pub. No.: WO2013/022806
PCT Pub. Date: Feb. 14, 2013

(65) Prior Publication Data
US 2014/0179962 A1 Jun. 26, 2014

Related U.S. Application Data

(60) Provisional application No. 61/515,947, filed on Aug. 7, 2011.

(51) Int. Cl.
*C07C 17/25* (2006.01)
*C07C 17/04* (2006.01)
*C07C 17/20* (2006.01)

(52) U.S. Cl.
CPC ............... *C07C 17/20* (2013.01); *C07C 17/04* (2013.01); *C07C 17/25* (2013.01)

(58) Field of Classification Search
CPC .............................. C07C 17/25; C07C 17/04
USPC .......................... 570/246, 247, 226, 227, 229
See application file for complete search history.

(56) References Cited

U.S. PATENT DOCUMENTS

| 2,119,484 A | 5/1938 | Levine |
| 2,179,378 A | 11/1939 | Metzger |
| 2,207,193 A | 7/1940 | Groll |

(Continued)

FOREIGN PATENT DOCUMENTS

| CH | 609022 | 6/1974 |
| CN | 101215220 | 7/2008 |

(Continued)

OTHER PUBLICATIONS

Levanova, S. V. et al. Doklaky Chemistry 2002, 386, pp. 496-498.*

(Continued)

*Primary Examiner* — Jafar Parsa
*Assistant Examiner* — Medhanit Bahta

(57) ABSTRACT

Processes for the production of chlorinated propenes are provided wherein a dehydrochlorination reaction occurs prior to a first chlorination reaction. The present processes make use of at least one reactor twice, i.e., at least two reactions occur in the same reactor. Cost and time savings are thus provided. Additional savings can be achieved by conducting more than two chlorination reactions, or all chlorination reactions, in one chlorination reactor, and/or by conducting more than two dehydrochlorination reactions, or all dehydrochlorination reactions, within a single dehydrochlorination reactor.

14 Claims, 3 Drawing Sheets

(56) References Cited

U.S. PATENT DOCUMENTS

| | | |
|---|---|---|
| 2,299,441 A | 10/1942 | Vaughan |
| 2,302,228 A | 11/1942 | Kharasch |
| 2,370,342 A | 2/1945 | Zellner |
| 2,378,859 A | 6/1945 | Martin |
| 2,435,983 A | 2/1948 | Schmerling |
| 2,449,286 A | 9/1948 | Fairbairn |
| 2,588,867 A | 3/1952 | Morris |
| 2,630,461 A | 3/1953 | Sachsse |
| 2,688,592 A | 9/1954 | Skeeters |
| 2,762,611 A | 9/1956 | Monroe |
| 2,765,359 A | 10/1956 | Pichler |
| 2,964,579 A | 12/1960 | Weller et al. |
| 2,973,393 A | 2/1961 | Monroe |
| 3,000,980 A | 9/1961 | Asadorian |
| 3,094,567 A | 6/1963 | Eaker |
| 3,112,988 A | 12/1963 | Coldren et al. |
| 3,444,263 A | 5/1969 | Fernald |
| 3,446,859 A | 5/1969 | Well |
| 3,502,734 A | 3/1970 | Baird |
| 3,525,595 A | 8/1970 | Zirngibl et al. |
| 3,551,512 A | 12/1970 | Loeffler |
| 3,558,438 A | 1/1971 | Schoenbeck |
| 3,651,019 A | 3/1972 | Asscher |
| 3,676,508 A | 7/1972 | Krekeler |
| 3,819,731 A | 6/1974 | Pitt |
| 3,823,195 A | 7/1974 | Smith |
| 3,872,664 A | 3/1975 | Lohmann |
| 3,914,167 A | 10/1975 | Ivy |
| 3,920,757 A | 11/1975 | Watson |
| 3,926,758 A | 12/1975 | Smith |
| 3,948,858 A | 4/1976 | Wiersum |
| 3,954,410 A | 5/1976 | Pohl |
| 4,038,372 A | 7/1977 | Colli |
| 4,046,656 A | 9/1977 | Davis et al. |
| 4,051,182 A | 9/1977 | Pitt |
| 4,319,062 A | 3/1982 | Boozalis et al. |
| 4,513,154 A | 4/1985 | Kurtz |
| 4,535,194 A | 8/1985 | Woodard |
| 4,614,572 A | 9/1986 | Holbrook |
| 4,644,907 A | 2/1987 | Hunter |
| 4,650,914 A | 3/1987 | Woodard |
| 4,661,648 A | 4/1987 | Franklin |
| 4,702,809 A | 10/1987 | Mueller |
| 4,714,792 A | 12/1987 | Muller |
| 4,716,255 A | 12/1987 | Muller |
| 4,726,686 A | 2/1988 | Wolf |
| 4,727,181 A | 2/1988 | Kruper |
| 4,849,554 A | 7/1989 | Cresswell et al. |
| 4,894,205 A | 1/1990 | Westerman |
| 4,902,393 A | 2/1990 | Muller |
| 4,999,102 A | 3/1991 | Cox |
| 5,057,634 A | 10/1991 | Webster |
| 5,132,473 A | 7/1992 | Furutaka |
| 5,171,899 A | 12/1992 | Furutaka |
| 5,178,844 A | 1/1993 | Carter et al. |
| 5,246,903 A | 9/1993 | Harley |
| 5,254,771 A | 10/1993 | Cremer |
| 5,254,772 A | 10/1993 | Dukat |
| 5,254,788 A | 10/1993 | Gartside |
| 5,262,575 A | 11/1993 | Dianis |
| 5,315,044 A | 5/1994 | Furutaka |
| 5,367,105 A | 11/1994 | Miyazaki et al. |
| 5,414,166 A | 5/1995 | Kim |
| 5,504,266 A | 4/1996 | Tirtowidjojo et al. |
| 5,684,219 A | 11/1997 | Boyce |
| 5,689,020 A | 11/1997 | Boyce |
| 5,811,605 A | 9/1998 | Tang |
| 5,895,825 A | 4/1999 | Elsheikh |
| 5,986,151 A | 11/1999 | Van Der Puy |
| 6,111,150 A | 8/2000 | Sakyu |
| 6,118,018 A | 9/2000 | Savidakis |
| 6,160,187 A | 12/2000 | Strickler |
| 6,187,976 B1 | 2/2001 | Van Der Puy |
| 6,229,057 B1 | 5/2001 | Jackson et al. |
| 6,235,951 B1 | 5/2001 | Sakyu et al. |
| 6,472,573 B1 | 10/2002 | Yamamoto |
| 6,518,467 B2 | 2/2003 | Tung et al. |
| 6,538,167 B1 | 3/2003 | Brown |
| 6,545,176 B1 | 4/2003 | Tsay |
| 6,551,469 B1 | 4/2003 | Nair |
| 6,610,177 B2 | 8/2003 | Tsay |
| 6,683,216 B1 | 1/2004 | Zoeller |
| 6,825,383 B1 | 11/2004 | Dewkar |
| 6,924,403 B2 | 8/2005 | Barnes et al. |
| 6,958,135 B1 | 10/2005 | Filippi |
| 7,117,934 B2 | 10/2006 | Lomax |
| 7,189,884 B2 | 3/2007 | Mukhopadhyay |
| 7,226,567 B1 | 6/2007 | Olbert |
| 7,282,120 B2 | 10/2007 | Braun |
| 7,297,814 B2 | 11/2007 | Yada |
| 7,345,209 B2 | 3/2008 | Mukhopadhyay |
| 7,371,904 B2 | 5/2008 | Ma |
| 7,378,559 B2 | 5/2008 | Verwijs |
| 7,396,965 B2 | 7/2008 | Mukhopadhyay |
| 7,511,101 B2 | 3/2009 | Nguyen |
| 7,521,029 B2 | 4/2009 | Guetlhuber |
| 7,588,739 B2 | 9/2009 | Sugiyama |
| 7,659,434 B2 | 2/2010 | Mukhopadhyay |
| 7,674,939 B2 | 3/2010 | Mukhopadhyay |
| 7,687,670 B2 | 3/2010 | Nappa |
| 7,695,695 B2 | 4/2010 | Shin |
| 7,714,177 B2 | 5/2010 | Mukhopadhyay |
| 7,836,941 B2 | 11/2010 | Song |
| 7,880,040 B2 | 2/2011 | Mukhopadhyay |
| 7,951,982 B2 | 5/2011 | Mukhopadhyay |
| 8,058,486 B2 | 11/2011 | Merkel |
| 8,058,490 B2 | 11/2011 | Strebelle |
| 8,071,825 B2 | 12/2011 | Johnson |
| 8,071,826 B2 | 12/2011 | Van Der Puy |
| 8,076,521 B2 | 12/2011 | Elsheikh |
| 8,084,653 B2 | 12/2011 | Tung |
| 8,115,038 B2 | 2/2012 | Wilson |
| 8,123,398 B2 | 2/2012 | Teshima |
| 8,158,836 B2 | 4/2012 | Pigamo |
| 8,232,435 B2 | 7/2012 | Sievert |
| 8,258,353 B2 | 9/2012 | Kruper |
| 8,258,355 B2 | 9/2012 | Merkel |
| 8,357,828 B2 | 1/2013 | Okamoto |
| 8,367,867 B2 | 2/2013 | Zardi |
| 8,383,867 B2 | 2/2013 | Mukhopadhyay |
| 8,395,000 B2 | 3/2013 | Mukhopadhyay |
| 8,398,882 B2 | 3/2013 | Rao et al. |
| 8,487,146 B2 | 7/2013 | Wilson |
| 8,558,041 B2 | 10/2013 | Tirtowidjojo et al. |
| 8,581,011 B2 | 11/2013 | Tirtowidjojo |
| 8,581,012 B2 | 11/2013 | Tirtowidjojo et al. |
| 8,614,361 B2 | 12/2013 | Suzuki |
| 8,614,363 B2 | 12/2013 | Wilson et al. |
| 8,907,148 B2 | 12/2014 | Tirtowidjojo et al. |
| 8,926,918 B2 | 1/2015 | Tirtowidjojo et al. |
| 8,933,280 B2 | 1/2015 | Tirtowidjojo et al. |
| 8,957,258 B2 | 2/2015 | Okamoto et al. |
| 9,056,808 B2 | 6/2015 | Tirtowidjojo et al. |
| 9,067,855 B2 | 6/2015 | Grandbois et al. |
| 2001/0018962 A1 | 9/2001 | Joshi |
| 2002/0110711 A1 | 8/2002 | Boneberg |
| 2006/0150445 A1 | 7/2006 | Redding |
| 2006/0292046 A1 | 12/2006 | Fruchey |
| 2007/0197841 A1 | 8/2007 | Mukhopadhyay |
| 2007/0265368 A1 | 11/2007 | Rao |
| 2008/0021229 A1 | 1/2008 | Maughon |
| 2008/0073063 A1 | 3/2008 | Clavenna et al. |
| 2008/0118018 A1 | 5/2008 | Schrauwen |
| 2008/0207962 A1 | 8/2008 | Rao |
| 2009/0018377 A1 | 1/2009 | Boyce |
| 2009/0030249 A1* | 1/2009 | Merkel et al. ............. 570/227 |
| 2009/0088547 A1 | 4/2009 | Schamschurin et al. |
| 2009/0099396 A1 | 4/2009 | Mukhopadhyay |
| 2009/0117014 A1 | 5/2009 | Carpenter |
| 2009/0203945 A1 | 8/2009 | Mukhopadhyay |
| 2010/0041864 A1 | 2/2010 | Kadowaki et al. |
| 2010/0185029 A1 | 7/2010 | Elsheikh |
| 2010/0263278 A1 | 10/2010 | Kowoll et al. |
| 2011/0087056 A1 | 4/2011 | Tirtowidjojo et al. |

(56) References Cited

U.S. PATENT DOCUMENTS

| | | |
|---|---|---|
| 2011/0172472 A1 | 7/2011 | Sakyu |
| 2011/0218369 A1 | 9/2011 | Elsheikh |
| 2011/0251425 A1 | 10/2011 | Penzel |
| 2012/0065434 A1 | 3/2012 | Nose |
| 2014/0081055 A1 | 3/2014 | Tirtowidjojo |
| 2014/0163266 A1 | 6/2014 | Tirtowidjojo et al. |
| 2014/0179962 A1 | 6/2014 | Tirtowidjojo et al. |
| 2014/0323775 A1 | 10/2014 | Grandbois et al. |
| 2014/0323776 A1 | 10/2014 | Grandbois et al. |
| 2014/0336425 A1 | 11/2014 | Tirtowdjojo et al. |
| 2014/0336431 A1 | 11/2014 | Tirtowidjojo et al. |
| 2014/0371494 A1 | 12/2014 | Tirtowidjojo et al. |
| 2015/0045592 A1 | 2/2015 | Grandbois et al. |
| 2015/0057471 A1 | 2/2015 | Tirtowidjojo et al. |
| 2015/0217256 A1 | 8/2015 | Tirtowidjojo et al. |

FOREIGN PATENT DOCUMENTS

| | | |
|---|---|---|
| CN | 101492341 | 7/2009 |
| CN | 101544535 | 9/2009 |
| CN | 101597209 | 12/2009 |
| CN | 101913979 | 12/2010 |
| CN | 101913980 | 12/2010 |
| CN | 101955414 | 1/2011 |
| CN | 101982227 | 3/2011 |
| CN | 102001911 | 4/2011 |
| CN | 102249846 | 11/2011 |
| CN | 102351637 | 2/2012 |
| DE | 857955 | 12/1952 |
| DE | 209184 | 4/1984 |
| DE | 235631 | 5/1986 |
| DE | 102005044501 | 3/2007 |
| DE | 102010022414 | 12/2011 |
| EP | 0164798 | 12/1985 |
| EP | 0453818 | 10/1991 |
| EP | 1018366 | 12/2000 |
| EP | 1097984 A1 | 5/2001 |
| FR | 1546709 | 11/1968 |
| GB | 471186 | 8/1937 |
| GB | 471187 | 8/1937 |
| GB | 471188 | 8/1937 |
| GB | 857086 | 12/1960 |
| GB | 1134585 | 11/1968 |
| GB | 1381619 | 1/1975 |
| GB | 1548277 | 7/1979 |
| JP | 54-079207 | 6/1979 |
| JP | S54-135712 | 10/1979 |
| JP | 08-119885 | 5/1996 |
| JP | 2001-151708 | 6/2001 |
| JP | 2001-213820 | 8/2001 |
| JP | 2006-272267 A | 10/2006 |
| JP | 2007-021396 | 2/2007 |
| JP | 2008-063314 | 3/2008 |
| JP | 2009-000592 A | 1/2009 |
| JP | 2009-046653 | 3/2009 |
| JP | 2011-144148 | 7/2011 |
| LU | 52247 | 12/1996 |
| SU | 899523 | 1/1982 |
| WO | 0138271 | 5/2001 |
| WO | 0138275 | 5/2001 |
| WO | 02059536 A1 | 8/2002 |
| WO | 2005016509 | 2/2005 |
| WO | 2007079431 | 7/2007 |
| WO | 2007079435 | 7/2007 |
| WO | 2007096383 | 8/2007 |
| WO | 2009015304 | 1/2009 |
| WO | 2009067571 | 5/2009 |
| WO | 2009087423 | 7/2009 |
| WO | 2011060211 | 5/2011 |
| WO | 2011065574 | 6/2011 |
| WO | 2012011844 | 1/2012 |
| WO | 2012081482 | 6/2012 |
| WO | 2012166393 | 12/2012 |
| WO | 2013082410 | 6/2013 |
| WO | 2014046970 | 3/2014 |
| WO | 2014046977 | 3/2014 |
| WO | 2014066083 | 5/2014 |
| WO | 2014100039 | 6/2014 |
| WO | 2014100066 | 6/2014 |
| WO | 2014134233 | 9/2014 |
| WO | 2014134377 | 9/2014 |
| WO | 2014164368 | 10/2014 |

OTHER PUBLICATIONS

Bai et al., "Isomerization of Tetrachloropropene to Promote Utilization Ratio of Triallate Raw Materials", Petrochemical Technology & Application, 2007, 25(1).

Boualy et al., "Kharasch Addition of Tetrachloromethane to Alkenes Catalyzed by Metal Acetylacetonates", Catalysis Communications, 2011, pp. 1295-1297, vol. 12.

Chai et al., "Study of Preparation of 1,1,1,3-tetrachloropropane", Zhejiang Chemical Industry, 2010, pp. 1-3, 41(5).

Cristiano et al., "Tetraalkylphosphonium Trihalides. Room Temperature Ionic Liquids As Halogenation Reagents", J. Org. Chem., 2009, pp. 9027-9033, vol. 74.

Evstigneev et al., "Initiated Chlorination of Tetrachloropropane", Khim. Prom., 1984, pp. 393-394, 16(7).

Galitzenstein et al., "The Dehydrochlorination of Propylene Dichloride", Journal of the Society of Chemical Industry, 1950, pp. 298-304, vol. 69.

Gault et al., "Chlorination of Chloroform", Comptes Rendus Des Seances De L'Academie des Sciences, 1924, pp. 467-469, vol. 179.

Gerding et al., "Raman Spectra of aliphatic chlorine compounds II. Chloroethenes and Chloropropenes", RECUEIL, Jan. 1, 1955, pp. 957-975, vol. 74.

Hatch et al., "Allylic Chlorides. XV. Preparation and Properties of the 1,2,3-Trichloropropenes", JACS, Jan. 5, 1952, pp. 123-126, 74(1).

Hatch et al., "Allylic Chlorides. XVIII. Preparation and Properties of 1,1,3-tricholoro-2-fluoro-1-propene and 1,1,2,3-tetracholoro-1-propene", JACS, Jul. 5, 1952, pp. 3328-3330, 74(13).

Herzfelder, "Substitution in the Aliphatic Series", Berichte der Deutschen Chemischen Gesellschaft, May-Aug. 1893, pp. 1257-1261, 26(2).

Ivanov et al., "Metal Phthalocyanine-Catalyzed Addition of Polychlorine-Containing Organic Compounds to C=C Bonds", Russian Chemical Bulletin, International Edition, Nov. 2009, pp. 2393-2396, 58(11).

Kang et al., "Kinetics of Synthesis of 1,1,1,3,3-pentachlorobutane Catalyzed by Fe—FeCl3", Chemical Research and Application, Jun. 2011, pp. 657-660, 23(6).

Kharasch et al., "Chlorinations with Sulfuryl Chloride. I. The Peroxide-Catalyzed Chlorination of Hydrocarbons", JACS, 1939, pp. 2142-2150, vol. 61.

Khusnutdinov et al., "CCl4 Attachment to Olefins Catalyzed by Chromium and Ruthenium Complexes. Impact of Water as a Nucleophilic Admixture", Oil Chemistry, 2009, pp. 349-356, vol. 4.

Kruper et al., "Synthesis of alpha-Halocinnamate Esters via Solvolytic Rearrangement of Trichloroallyl Alcohols", J. Org. Chem., 1991, pp. 3323-3329, vol. 56.

Leitch, "Organic Deuterium Compounds: V. The chlorination of propyne and propyne D-4", Canadian Journal of Chemistry, Apr. 1, 1953, pp. 385-386, 30(4).

Levanova et al., "Thermocatalytic Reactions of Bromochloropropanes", Russian Journal of Physical Chemistry, Jan. 1, 1983, pp. 1142-1146, vol. 57.

Liu et al., "Progress in the Synthesis of 1,1,1,3-tetrachloropropane", Guangzhou Chemicals, 2011, pp. 41-42, 39(5).

McBee et al., "Utilization of Polychloropropanes and Hexachloroethane", Industrial and Engineering Chemistry, Feb. 1, 1941, pp. 176-181, 33(2).

Mouneyrat, "Effect of Chlorine on Propyl Chloride in the Presence of Anhydrous Aluminum Chloride" Bulletin de la Societe Chimique de Paris, Jan. 1, 1899, pp. 616-623, 3(21).

Munoz-Molina et al., "An Efficient, Selective and Reducing Agent-Free Copper Catalyst for the Atom-Transfer Radical Addition of Halo Compounds to Activated Olefins", Inorg. Chem., 2010, pp. 643-645, 49.

(56) References Cited

OTHER PUBLICATIONS

Nair et al., "Atom Transfer Radical Addition (ATRA) of Carbon Tetrachloride and Chlorinated Esters to Various Olefins Catalyzed by CP'Ru(PPh3)(PR3)Cl Complexes", Inorganica Chimica Acta, 2012, pp. 96-103, vol. 380.

Nikishin et al., "Reactions of Methanol and Ethanol", Seriya Khimicheskaya, Dec. 1966, pp. 2188-2192, vol. 12.

Pozdnev et al., "Chlorination of Chloroform and the Conversion of Methylene Chloride Manufacture Still Residues", Khim., Khim. Tekhnol., 1970, 70(4).

Rotshtein et al., "Isomer Distribution on Chlorination of Chloropropanes", Zhurnal Organicheskoi Khimii, Sep. 1966, pp. 1539-1542, 2(9).

Semenov et al., "Selectivity of Photochemical Chlorination of Chloromethane in the Liquid Phase", Zhurnal Prikladnoi Khimii, Apr. 1985, pp. 840-845, 58(4).

Skell et al., "Reactions of BrCl with Alkyl Radicals", Tetrahedron Letters, 1986, pp. 5181-5184, 27(43).

Skell et al., "Selectivities of pi and sigma-Succinimidyl Radicals in Aubstitution and Addition Reactions. Appendix: Response to Walling, El-Taliawi and Zhao", JACS, Jul. 1, 1983, pp. 5125-5131, 105(15).

Tanuma et al., "Partially Fluorinated Metal Oxide Catalysts for a Friedel-Crafts-type Reaction of Dichlorofluoromethane with Tetrafluoroethylene", Catalysis Letters, 2010, pp. 77-82, vol. 136.

Urry et al., "Free-Radical Reactions of Diazomethane with Reactive Bromopolychloroalkanes", JACS, May 5, 1964, pp. 1815-1819, 86(9).

Wang, "Elimination Reactions of Polyhalopropanes under Emulsion Catalytic Conditions to give Halopropenes", Synthesis, Jun. 1982, pp. 494-496, vol. 6.

Zhao et al, "Research Progress on Preparation Technology of 1,1,2,3-Tetrachloropropene", Zhejiang Chemical Industry, 2010, pp. 8-10, 41(8).

Zheng et al., "Review of the Preparation of the low GWP alternative 1,3,3,3-tetrafluoropropene", Zhejiang Chemical Industry, 2010, pp. 5-7, 41(3).

Ochi, et al., "Preparation of Chloropropenes by Photochemical Dehydrochlorination of 1,2-Dichloropropane", Chemical Abstracts, Jul. 17, 1989, p. 574, 111(3).

Stevens, "Some New Cyclopropanes with a Note on the Exterior Valence Angles of Cyclopropane", JACS, Vo. 68, No. 4, 1945, 620-622.

Fields et al., "Thermal Isomerization of 1,1-dichlorocyclopropanes", Chemical Communications (London) No. 21, Jan. 1, 1967, p. 1081.

Nguyen et al., Condensation de chloroforme avec des olefins fluorees en milieu basique, Journal of Fluorine Chemistry, vol. 55, No. 3, Dec. 1, 1991, pp. 241-248.

Shelton et al., "Addition of Halogens and Halogen Compounds to Allylic Chlorides. I. Addition of Hydrogen Halides", Journal of Organic Chemistry, Sep. 1958, pp. 1876-1880, vol. 23.

Tobey et al., "Pentachlorocyclopropane 1" Journal of the American Chemical Society, vol. 88, No. 11, Jun. 1, 1996 pp. 2478-2481.

Michigan Technological Univ., "Free-Radical Chlorination with Sulfuryl Chloride", Nov. 15, 2001, 1-7.

\* cited by examiner

PROCESS FOR THE PRODUCTION OF CHLORINATED PROPENES

FIELD

The present invention relates to processes for the production of chlorinated propenes.

BACKGROUND

Hydrofluorocarbon (HFC) products are widely utilized in many applications, including refrigeration, air conditioning, foam expansion, and as propellants for aerosol products including medical aerosol devices. Although HFC's have proven to be more climate friendly than the chlorofluorocarbon and hydrochlorofluorocarbon products that they replaced, it has now been discovered that they exhibit an appreciable global warming potential (GWP).

The search for more acceptable alternatives to current fluorocarbon products has led to the emergence of hydrofluoroolefin (HFO) products. Relative to their predecessors, HFOs are expected to exert less impact on the atmosphere in the form of a lesser, or no, detrimental impact on the ozone layer and their much lower GWP as compared to HFC's. Advantageously, HFO's also exhibit low flammability and low toxicity.

As the environmental, and thus, economic importance of HFO's has developed, so has the demand for precursors utilized in their production. Many desirable HFO compounds, e.g., such as 2,3,3,3-tetrafluoroprop-1-ene or 1,3,3,3-tetrafluoroprop-1-ene, may typically be produced utilizing feedstocks of chlorocarbons, and in particular, chlorinated propenes, which may also find use as feedstocks for the manufacture of polyurethane blowing agents, biocides and polymers.

Unfortunately, many chlorinated propenes may have limited commercial availability, and/or may only be available at prohibitively high cost, due at least in part to the complicated, multi-step processes typically utilized in their manufacture. For example, in methods that utilize allyl chloride or 1,2,3-trichloropropane (TCP) as starting materials, successive dehydrochlorinations and chlorinations with elemental chlorine may be done until the desired number of chlorine atoms has been added. Or, some conventional methods call for the chlorination of chlorinated alkanes having fewer chlorine atoms than desired in the final product.

Such multistep reactions are typically carried out as batch and/or semi-batch processes, and thus can suffer from low production capacity. In addition to the multiple reaction steps, such processes may also require purification steps to be carried out either between or after the reaction steps making these multistep processes very capital intensive. Further, such processes may also result in the production of large amounts of contaminated waste water having high quantities of sodium chloride, and one or more chlorinated organic(s). The waste water thus must typically be treated before releasing it to the environment, requiring even further expenditure. Any recovered sodium chloride provides little in the way of recoverable cost.

It would thus be desirable to provide improved processes for the large capacity and/or continuous production of chlorocarbon precursors useful as feedstocks in the synthesis of refrigerants and other commercial products. More particularly, such processes would provide an improvement over the current state of the art if they were less costly not only in processing time, but capital costs required to implement and maintain the process. Generation of byproducts having a higher value than sodium chloride, or really any value, would be a further advantage if provided in such a process.

BRIEF DESCRIPTION

The present invention provides efficient processes for the production of chlorinated propenes. Advantageously, and although the processes utilize 1,2,3-trichloropropane as a starting material, the processes nonetheless provide substantial time and cost savings by requiring fewer steps, and/or fewer reactors, to conduct them in. Furthermore, the processes may make use of at least one catalytic dehydrochlorination step, in place of one or more caustic dehydrochlorination step(s), and so waste water production is minimized, as is the production of the low-value by-product sodium chloride. Finally, the processes start with a dehydrochlorination step, and as a result, the first chlorination occurs across a double bond. As a result, catalysts may not be required for this step, and further cost savings can be seen.

In one aspect, the present invention provides a process for the production of chlorinated propenes from 1,2,3-trichloropropane wherein a dehydrochlorination step occurs prior to a first chlorination step and at least two reactions are carried out in the same reactor. The dehydrochlorination reactions may occur in either the vapor or liquid phase and may be carried out in the presence of a dehydrochlorination catalyst, i.e., $FeCl_3$, $Cr_2O_3$, activated carbon, or combinations of these. One or more of the dehydrochlorination reactions can also be carried out in the liquid phase by reaction with aqueous caustic. At least two chlorination reactions, or at least two dehydrochlorination reactions, may occur in the same reactor, or in some advantageous embodiments, all of the chlorination reactions and/or all of the dehydrochlorination reactions may occur in the same reactor. Although catalysts may not be required for the chlorination step in all embodiments, their use may provide advantages in others, and in such embodiments, ionic chorination catalysts or free radical initiators are desirably utilized.

The chlorination agent may comprise chlorine, $SO_2Cl_2$, or combinations of these. The chlorinated propene produced desirably comprises from 3 to 5 chlorine atoms, and in some embodiments, may be 1,1,2,3-tetrachloropropene. In some embodiments, HCl is generated by the process as a by-product, and may be recovered in its anhydrous form for use, e.g., in downstream processes. Further, one or more reactants may be generated within or upstream of the process.

The advantages provided by the present processes may be carried forward by utilizing the chlorinated propenes to produce further downstream products, such as, e.g., 2,3,3,3-tetrafluoroprop-1-ene or 1,3,3,3-tetrafluoroprop-1-ene.

DETAILED DESCRIPTION

Figure 1:
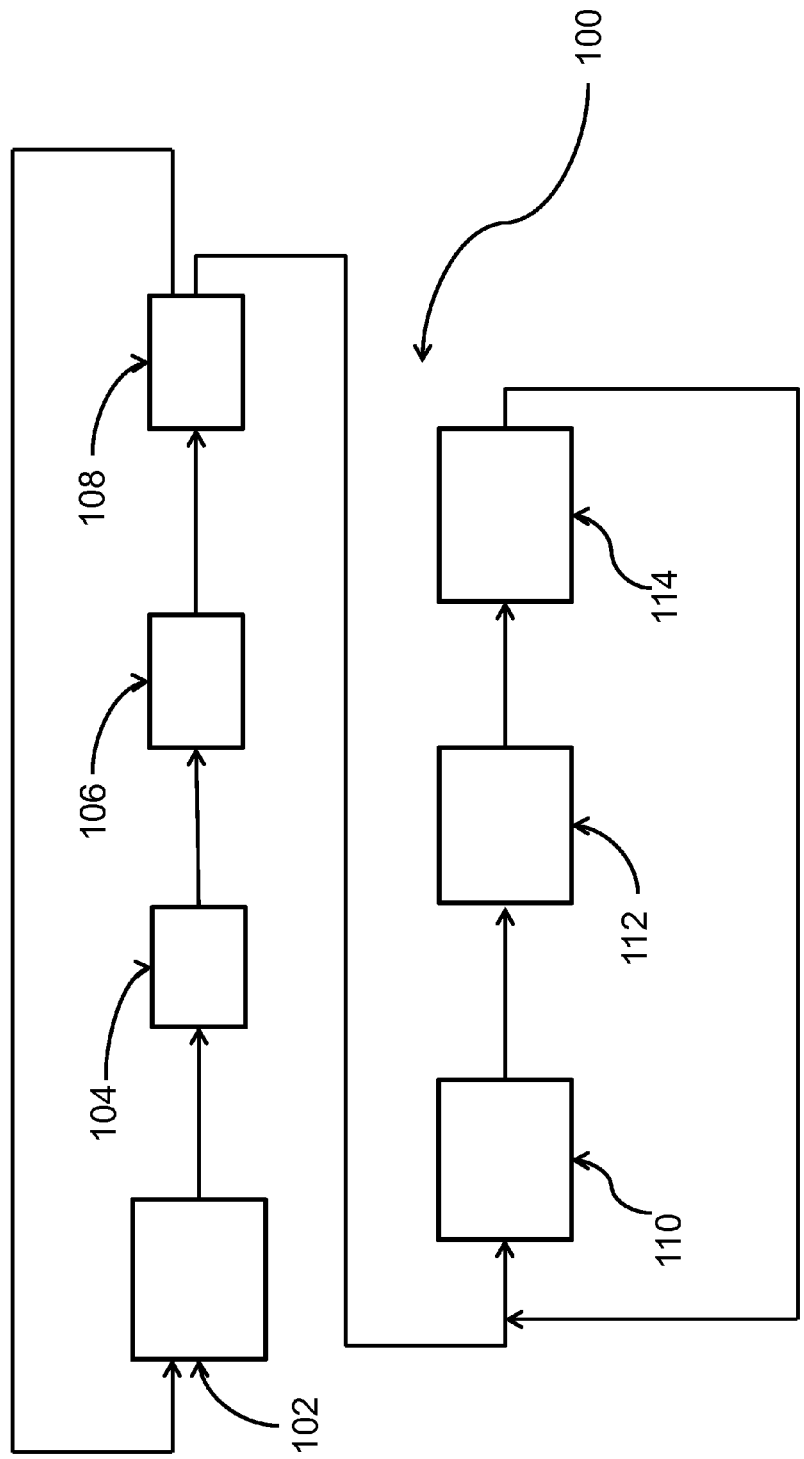
FIG. 1 is a schematic diagram of a process according to one embodiment.

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

If ranges are disclosed, the endpoints of all ranges directed to the same component or property are inclusive and independently combinable (e.g., ranges of "up to 25 wt. %, or, more specifically, 5 wt. % to 20 wt. %," is inclusive of the endpoints and all intermediate values of the ranges of "5 wt. % to 25 wt. %," etc.). As used herein, percent (%) conversion is meant to indicate change in molar or mass flow of reactant in a reactor in ratio to the incoming flow, while percent (%) selectivity means the change in molar flow rate of product in a reactor in ratio to the change of molar flow rate of a reactant.

Reference throughout the specification to "one embodiment" or "an embodiment" means that a particular feature, structure, or characteristic described in connection with an embodiment is included in at least one embodiment. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

In some instances, "TCP" may be used herein as an abbreviation for 1,2,3-trichloropropane, "ACL" may be used as an abbreviation for allyl chloride or 3-chloropropene, and "TCPE" may be used as an abbreviation for 1,1,2,3-tetrachloropropene. The terms "cracking" and "dehydrochlorination" are used interchangeably to refer to the same type of reaction, i.e., one resulting in the creation of a double bond typically via the removal of a hydrogen and a chlorine atom from adjacent carbon atoms in chlorinated hydrocarbon reagents.

The present invention provides efficient processes for the continuous production of chlorinated propenes from a feed stream comprising TCP wherein a dehydrochlorination step occurs first. The feedstream may additionally comprise one or more other chlorinated alkanes or alkenes, e.g., allyl chloride. The processes are not only advantageous in their ability to be run continuously, but also, since a dehydrochlorination step occurs first, the use of a catalyst in subsequent chlorination steps is not required and some embodiments may not make use of the same. However, the invention is not so limited, and in some instances, e.g., wherein an increase in reaction kinetics and throughput is desirable, chlorination catalysts may be utilized.

The present processes are further advantageous in that, at least two of the reactions desirably take place in the same reactor, and so time and cost savings are provided. As used herein, the phrase "at least two reactions" is meant to indicate two reactions involving at least one different reagent, rather than successive reactions of the same reagents. That is, "at least two chlorination reactions" is meant to indicate, e.g., the chlorination of 2,3 dichloropropene and 1,2,3 trichloropropene, rather than the multiple chlorinations of TCP that may typically occur in a continuous process. As a further example, "at least two dehydrochlorination reactions" is meant to indicate, e.g., the dehydrochlorination of TCP and the dehydrochlorination of a tetra- and/or a pentachloropropane isomer, rather than the multiple dehydrochlorinations of TCP that may typically occur in a continuous process.

Either two chlorination reactions may be conducted in the same chlorination reactor, or two dehydrochlorinations may be conducted in the same dehydrochlorination reactor, or both, or all of the chlorination reactions may take place in the same chlorination reactor and/or all dehydrochlorination reactions may take place in the same dehydrochlorination reactor, or both, or any combination there between. All the present invention requires is that at least two chlorination and/or at least two dehydrochlorination reactions take place in the same reactor to provide the benefits of lower capital costs, and processing time and hence higher capacity.

The present processes, in some embodiments, may also provide a reduction of caustic cracking steps as compared to conventional processes, and so, a greater amount of anhydrous HCl can be recovered. Anhydrous HCl is of greater value than the sodium chloride produced as a byproduct in conventional processes for the production of chlorinated propenes that typically employ multiple caustic cracking steps. These embodiments of the present process thus result in the production of a by-product that may either be sold or used as a feedstock for other processes, e.g., ethylene oxychlorination to produce ethylene dichloride.

In such embodiments, one or more of the dehydrochlorination steps of the present process may be carried out in the presence of a catalyst. Suitable dehydrochlorination catalysts include, but are not limited to, ferric chloride ($FeCl_3$). Other suitable examples of vapor phase dehydrochlorination catalysts known to those of ordinary skill in the art are disclosed in International Patent Application No. WO 2009/015304 A1.

In other embodiments, one or more of the dehydrochlorination steps of the present process may be conducted in the presence of a liquid caustic. Although vapor phase dehydrochlorinations advantageously result in the formation of a higher value byproduct than liquid phase dehydrochlorinations, liquid phase dehydrochlorination reactions can provide cost savings since evaporation of reactants is not required. The lower reaction temperatures used in liquid phase reactions may also result in lower fouling rates than the higher temperatures used in connection with gas phase reactions, and so reactor lifetimes may also be optimized when at least one liquid phase dehydrochlorination is utilized.

Many chemical bases are known in the art to be useful for liquid caustic cracking, and any of these can be used. For example, suitable cracking bases include, but are not limited to, alkali metal hydroxides, such as sodium hydroxide, potassium hydroxide, calcium hydroxide; alkali metal carbonates such as sodium carbonate; lithium, rubidium, and cesium or combinations of these. Phase transfer catalysts such as quaternary ammonium and quaternary phosphonium salts (e.g. benzyltrimethylammonium chloride or hexadecyltributylphosphonium bromide) can also be added to improve the dehydrochlorination reaction rate with these chemical bases.

The use of a dehydrochlorination step, prior to a chlorination step, advantageously can reduce, or eliminate, the need for the use of a catalyst for subsequent chlorination step. Nonetheless, chlorination catalysts can be used, if desired, in order to increase the reaction kinetics. For example, free radical catalysts or initiators may be used to enhance the present process. Such catalysts may typically comprise one or more chlorine, peroxide or azo- (R—N=N—R') groups and/ or exhibit reactor phase mobility/activity. As used herein, the phrase "reactor phase mobility/activity" means that a substantial amount of the catalyst or initiator is available for generating free radicals of sufficient energy which can initiate and propagate effective turnover of the product, the chlorinated and/or fluorinated propene(s), within the design limitations of the reactor.

Furthermore, the catalyst/initiator should have sufficient homolytic dissociation energies such that the theoretical maximum of free radicals is generated from a given initiator under the temperature/residence time of the process. It is especially useful to use free radical initiators at concentrations where free radical chlorination of incipient radicals is prevented due to low concentration or reactivity. Surprisingly, the utilization of the same, does not result in an increase in the production of impurities by the process, but does provide selectivities to the chlorinated propenes of at least 50%, or up to 60%, up to 70%, and in some embodiments, up to 80% or even higher.

Such free radical initiators are well known to those skilled in the art and have been reviewed, e.g., in "Aspects of some initiation and propagation processes," Bamford, Clement H. Univ. Liverpool, Liverpool, UK., Pure and Applied Chemistry, (1967), 15(3-4),333-48 and Sheppard, C. S.; Mageli, O. L. "Peroxides and peroxy compounds, organic," Kirk-Othmer Encycl. Chem. Technol., 3rd Ed. (1982), 17, 27-90.

Taking the above into consideration, examples of suitable catalysts/initiators comprising chlorine include, but are not limited to carbon tetrachloride, hexachloroacetone, chloroform, hexachloroethane, phosgene, thionyl chloride, sulfuryl chloride, trichloromethylbenzene, perchlorinated alkylaryl functional groups, or organic and inorganic hypochlorites, including hypochlorous acid, and t-butylhypochlorite, methylhypochlorite, chlorinated amines (chloramine) and chlorinated amides or sulfonamides such as chloroamine-T®, and the like. Examples of suitable catalysts/initiators comprising one or more peroxide groups include hydrogen peroxide, hypochlorous acid, aliphatic and aromatic peroxides or hydroperoxides, including di-t-butyl peroxide, benzoyl peroxide, cumyl peroxide and the like. Diperoxides offer an advantage of not being able to propagate competitive processes (e.g., the free radical chlorination of PDC to TCP (and its isomers) and tetrachloropropanes). In addition, compounds comprising azo- groups, such as azobisisobutyronitrile (AIBN), 1,1'-azobis(cyclohexanecarbonitrile)(ABCN), 2,2'-azobis(2,4-dimethyl valeronitrile), and dimethyl 2,2'-azobis(2-methylpropionate), may have utility in effecting the chlorination of PDC to trichloropropanes and tetrachloropropanes under the conditions of this invention. Combinations of any of these may also be utilized.

The process or reactor zone may be subjected to pulse laser or continuous UV/visible light sources at a wavelength suitable for inducing photolysis of the free radical catalyst/initiator, as taught by Breslow, R. in *Organic Reaction Mechanisms* W.A. Benjamin Pub, New York p 223-224. Wavelengths from 300 to 700 nm of the light source are sufficient to dissociate commercially available radical initiators. Such light sources include, e.g., Hanovia UV discharge lamps, sunlamps or even pulsed laser beams of appropriate wavelength or energy which are configured to irradiate the reactor chamber. Alternatively, chloropropyl radicals may be generated from microwave discharge into a bromochloromethane feedsource introduced to the reactor as taught by Bailleux et al., in Journal of Molecular Spectroscopy, 2005, vol. 229, pp. 140-144.

In some embodiments, ionic chlorination catalysts may be utilized in one or more chlorination steps and provide the advantage of dehydrochlorinating and chlorinating the subject alkane(s) at the same time. That is, ionic chlorination catalysts remove a chlorine and hydrogen from adjacent carbon atoms, the adjacent carbon atoms form a double bond, and HCl is released. A chlorine is then added back, replacing the double bond, to provide a more highly chlorinated alkane.

Ionic chlorination catalysts are well known to those or ordinary art and any of these may be used in the present process. Exemplary ionic chlorination catalysts include, but are not limited to, aluminum chloride, ferric chloride ($FeCl_3$) and other iron containing compounds, iodine, sulfur, antimony pentachloride ($SbCl_5$), boron trichloride ($BCl_3$), lanthanum halides, metal triflates, and combinations thereof.

Any or all of the dehydrochlorination or chlorination catalysts can be provided either in bulk or in connection with a substrate, such as activated carbon, graphite, silica, alumina, zeolites, fluorinated graphite and fluorinated alumina. Whatever the desired catalyst (if any), or format thereof, those of ordinary skill in the art are well aware of methods of determining the appropriate concentration and method of introduction thereof. For example, many catalysts are typically introduced into the reactor zone as a separate feed, or in solution with other reactants, e.g., TCP.

The amount of any dehydrochlorination catalyst and/or chlorination catalyst utilized will depend upon the particular catalyst chosen as well as the other reaction conditions. Generally speaking, in those embodiments of the invention wherein the utilization of a catalyst is desired, enough of the catalyst should be utilized to provide some improvement to reaction process conditions (e.g., a reduction in required temperature) or realized products, but yet not be more than will provide any additional benefit, if only for reasons of economic practicality.

For purposes of illustration only then, it is expected, that useful concentrations of an ionic chlorination catalyst or free radical initiator will range from 0.001% to 20% by weight, or from 0.01% to 10%, or from 0.1% to 5 wt. %, inclusive of all subranges there between. If a dehydrochlorination catalyst is utilized for one or more dehydrochlorination steps, useful concentrations may range from 0.01 wt. % to 5 wt. %, or from 0.05 wt. % to 2 wt. % at temperatures of from 70° C. to 200° C. If a chemical base is utilized for one or more dehydrochlorinations, useful concentrations of these will range from 0.01 to 12 grmole/L, or from 0.1 grmole/L to 5 grmole/L, or from 1 grmole/L to 2 grmole/L, inclusive of all subranges there between. Concentrations of each catalyst/base are given relative to the feed, e.g., 1,2,3-trichloropropane and/or allyl chloride.

The present process can make use of a feedstock comprising 1,2,3-trichloropropene to produce the desired chlorinated propenes. The process feedstock may also comprise allyl chloride, or other chlorinated alkanes, if desired. Whatever the composition of the feedstock, one or more of its components may be generated within the process, if desired, by any methods known to those of ordinary skill in the art.

The chlorination steps of the process may be carried out using any chlorination agent, and several of these are known in the art. For example, suitable chlorination agents include, but are not limited to chlorine, and/or sulfuryl chloride ($SO_2Cl_2$). Combinations of chlorinating agents may also be used. Either or both $Cl_2$ and sulfuryl chloride may be particularly effective when aided by the use of the aforementioned ionic chlorination catalysts.

Any chlorinated propene may be produced using the present method, although those with 3-5 chlorine atoms are more commercially attractive, and production of the same may thus be preferred in some embodiments. In some embodiments, the process may be used in the production of 1,1,2,3-tetrachloropropene, which may be a preferred feedstock for refrigerants, polymers, biocides, etc.

In additional embodiments, one or more reaction conditions of the process may be optimized, in order to provide even further advantages, i.e., improvements in selectivity, conversion or production of reaction by-products. In certain embodiments, multiple reaction conditions are optimized and even further improvements in selectivity, conversion and production of reaction by-products produced can be seen.

Reaction conditions of the process that may be optimized include any reaction condition conveniently adjusted, e.g., that may be adjusted via utilization of equipment and/or materials already present in the manufacturing footprint, or that may be obtained at low resource cost. Examples of such conditions may include, but are not limited to, adjustments to temperature, pressure, flow rates, molar ratios of reactants, etc.

That being said, the particular conditions employed at each step described herein are not critical, and are readily determined by those of ordinary skill in the art. What is important is that a dehydrochlorination reaction occurs prior to a first chlorination reaction, and that at least two reactions are carried out in the same vessel, i.e., two chlorination reactions, or two dehydrochlorination reactions are carried out in a single reactor. Those of ordinary skill in the art will readily be able to determine suitable equipment for each step, as well as the particular conditions at which the chlorination, dehydrochlorination, separation, drying and isomerization steps may be conducted.

In the present process, a feed stream comprising fresh 1,2,3-trichloropropane, either alone, or in some embodiments, in combination with allyl chloride, and/or recycled TCP, tetrachloropropanes and/or pentachloropropanes, is converted to TCPE using a series of consecutive dehydrochlorination and chlorination reactions, at least two of which occur in the same reactor.

In one exemplary embodiment, a fee stream comprising TCP is first fed to a vapor phase dehydrochlorination reactor, e.g., such as a continuous long reaction tubing arranged in a coil and heated in a fired box. A shell and multitube reactor wherein the tubes are filled with a fixed bed catalyst suitable for catalytically cracking the TCP can also be used. For reasons of process efficiency, the use of a reactor capable of accommodating a continuous process is preferred.

Suitable reaction conditions for this initial vapor-phase dehydrochlorination reactor include, e.g., temperatures of from ambient temperature (e.g., 200° C.) to 700° C., or from 250° C. to 600° C., or from 300° C. to 500° C. Ambient pressure may be used, or pressures of from 100 kPa to 1000 kPa, or from 100 kPa to 500 kPa, or from 100 kPa to 300 kPa. At such conditions, the dehydrochlorination of TCP will produce HCl, 2,3-dichloropropene, 1,2,3-trichloropropene and unreacted TCP.

Alternatively, a liquid phase dehydrochlorination reactor can be used in place of the vapor phase dehydrochlorination reactor, wherein liquid caustic can be used to convert TCP, alone or in combination with other tri-, tetra-, and pentachlorinated propane intermediates, to dichloro-, trichloro-, and tetrachloropropenes, respectively. Conditions of a caustic cracking reactor that will provide such a reaction are either well-known, or readily determined, by those of ordinary skill in the art. Generally speaking, a caustic dehydrochlorination reactor may be charged with caustic soda at 50% aqueous solution with a slight molar excess of caustic compared to the tri- and tetrachlorinated propane(s) and operated at pressures of from ambient to 400 kPA, temperatures of from 40° C. to 150° C., or from 60° C. to 120° C. and with residence times of less than 3 hours. Caustic dehydrochlorinations may be carried out with or without the use of phase transfer agent catalysts.

In those embodiments wherein the first dehydrochlorination is conducted in the vapor phase, the product stream is feed to a first separation column, e.g., a distillation column, operated at conditions effective to provide anhydrous HCl to an overhead line thereof. In those embodiments wherein the first dehydrochlorination is conducted in the liquid phase, the product stream thereof is typically provided to a drying column.

In the case of the former, the top temperature of a separation column for the recovery of anhydrous HCl may typically be set below 0° C. or more preferably, can be set at a temperature of from −70° C. to −10° C. The bottom temperature of such a column is desirably set at from 10° C. to 150° C., or from 30° C. to 100° C., with the exact temperature dependent to some degree on the bottom mixture composition, as will be understood by those of ordinary skill in the art. The pressure of this purification column is desirably set above 200 kPa or preferably, from 350 kPa to 2000 kPa, or more preferably from 500 kPa to 1000 kPa. The bottom stream of a column operated at such conditions would be expected to contain excess chlorine, unreacted TPC and monochloropropene intermediates, while the overhead stream would be expected to comprise anhydrous HCl.

The bottom stream of the anhydrous HCl recovery column may be either directly fed to a chlorination reactor, or fed to a further separation column, as desired, according to the particular embodiment being practiced.

One example of a suitable liquid phase chlorination reactor would be a batch or continuous stirred tank reactor with an internal cooling coil. A shell and multitube exchanger followed by vapor liquid disengagement tank or vessel can also be used. The suitable reaction conditions for liquid phase chlorinations include, e.g., temperatures of from ambient temperature (e.g., 20° C.) to 200° C., or from 30° C. to 150° C., or from 40° C. to 120° C. or from 50° C. to 100° C. Ambient pressure, or pressures of from 100 kPa to 1000 kPa, or from 100 kPa to 500 kPa, or from 100 kPa to 300 kPa may be used. In some embodiments, one or more catalysts comprising $FeCl_3$ or $AlCl_3$ may be used in the chlorination reactor, while in others, their use is without benefit.

Allyl chloride can be added to the chlorination reactor and when added, is chlorinated to trichloropropane, at conversions of greater than 60%, or 70%, or 80%, or 85%, or 90% or 95%, or even up to 100%. In such embodiments, the chlorination reactor is expected to produce a product stream comprising 1,2,2,3-tetrachloropropane and 1,1,2,2,3-pentachloropropane.

The liquid phase chlorinations may be carried out neat, i.e., in the absence of solvent, or, one or more solvents may be provided to the chlorination reactor, and may be provided as feedstock, or, recycled from one or more separation columns operably disposed to receive streams from the chlorination reactor. For example, monochloropropene intermediates may be recycled back to the chlorination reactor from one separation column and/or tri-and tetrachloropropene intermediates may be recycled from another separation column. Or, the chlorination reactor may be provided with a feedstock of any appropriate solvent for chlorination reactions, such as, e.g., carbon tetrachloride, sulfuryl chloride, 1,1,2,3,3-pentachloropropane, 1,1,2,2,3,3-hexachloropropane, other hexachloropropane isomers, or a combination of these.

In some embodiments, the bottoms stream from the HCl recovery column may be fed to a separation column, prior to being fed to a chlorination reactor. In such embodiments, the separation column would desirably be operated at conditions sufficient to produce an overhead stream of 1,2,3-trichloropropane and other chlorinated propanes to the chlorination reactor, while the bottoms stream therefrom, typically comprising 1,1,2,3-TCPE, 1,1,2,2,3-pentachloropropane and 1,2,2,3-tetrachloropropane, may be fed to a separation column for the recovery of 1,1,2,3-TCPE in an overhead stream thereof, and the recycle of the 1,1,2,3-pentachloropropane and 1,2,2,3-tetrachloropropane in a bottoms stream thereof to the vapor phase dehydrochlorination reactor.

In some embodiments, the liquid product stream from the chlorination reactor may be fed to a separation column prior to being recycled to the dehydrochlorination reactor, while in those wherein a refining step is carried out prior to the chlorination reactor, the liquid product stream may simply be directly recycled to the dehydrochlorination reactor. In the case of the former, the separation column is desirably operated at conditions effective to separate the tri- and tetra-chlorinated propanes from the pentachlorinated propanes. The overhead stream from this separation column, comprising tri- and tetra-chlorinated propanes, may be recycled back to the dehydrochlorination reactor to produce chlorinated propene intermediates, while the bottom stream, expected to comprise pentachloropropanes, e.g., 1,1,2,2,3 pentachloropropane, and heavier by-products is then sent to a further vapor phase dehydrochlorination reactor operated at conditions effective to produce a product stream comprising 1,1,2,3-TCPE.

The reaction stream from the second vapor phase dehydrochlorination reactor, comprising 1,1,2,3-TCPE, may optionally be provided to a separation column to remove HCl and other lighter byproduct than tetrachloropropenes, and the stream therefrom provided to a further reactor to isomerize any 2,3,3,3-tetrachloropropene to 1,1,2,3-tetrachloropropene under the appropriate conditions. For example, catalysts may be utilized to assist in the isomerization, in which case, suitable catalysts include, but are not limited to (i) siliceous granules having a polar surface including kaolinite, bentonite, and attapulgite; (ii) other mineral salts of silica such as saponite, quartz, (iii) siliceous non-mineral substance such as silica gel, fumed silica, and glass, or combinations of any of these. Suitable conditions for drying columns for such reaction streams are also known to those of ordinary skill in the art, as evidenced by U.S. Pat. No. 3,926,758.

In the case of those embodiments of the process wherein the dehydrochlorination are desirably carried out in the liquid phase, i.e., via caustic base, anhydrous HCl is not produced, and so, an HCl recovery column is not utilized. Even though NaCl is generated in such embodiments rather than anhydrous HCl, these embodiments are yet simplified compared to conventional process at least because they require less equipment—multiple, or all, dehydrochlorinations can occur in the same reactor. Instead of the product stream from the dehydrochlorination reactor being provided to an anhydrous HCl recovery column, the product stream is provided to a drying column. The dried stream, comprising 1,1,2,3-TCPE and di-, tri- and other tetrachloropropenes, is then provided to a distillation column operated at conditions sufficient to separate the dichloropropenes and trichloropropenes from the tetrachloropropenes. The dichloropropenes and trichloropropenes may then be fed to a chlorination reactor to produce tetra- and pentachloropropenes, while the tetrachloropropenes may be fed to a refining column operable to provide a stream of refined 1,1,2,3-TCPE as an overhead stream. The remainder of the stream of tetrachloropropenes is disposed of as waste.

A schematic illustration of one embodiment of the process is shown in FIG. 1. As shown in FIG. 1, process 100 would make use of vapor phase dehydrochlorination reactors 102 and 110, separation columns 104, 108, 112 and 114, and chlorination reactor 106. In operation, 1,2,3-trichloropropane is fed into gas-phase dehydrochlorination reactor 102, which is desirably operated at conditions sufficient to produce HCl, dichloropropenes, 1,2,3 trichloropropene and unreacted chloropropanes. This reaction stream is fed to separation column 104 for the recovery of HCl in the overhead stream.

The bottoms stream from separation column 104 is fed to chlorination reactor 106, which produces a reaction stream comprising tetrachloropropanes and pentachloropropanes. Unreacted 1,2,3 TCP and 1,2,2,3 tetrachloropropane in the product stream from chlorination reactor 106 are recovered by separation column 108 and recycled to gas-phase dehydrochlorination reactor 102. The 1,1,2,2,3 pentachloropropane produced by chlorination reactor 106 is separated as a bottoms stream from separation column 108 and sent to second dehydrochlorination reactor 110.

The product stream from dehydrochlorination reactor 110, comprising TCPE, unreacted pentachloropropanes and HCL is provided to separation column 112, which may produce an overhead stream comprising additional anhydrous HCl. The bottom stream from separation column 112, comprising 1,1,2,3-TCPE and unreacted pentachloropropanes, is provided to separation column 114. Separation column 114 provides a product stream comprising TCPE and recycles the unreacted pentachloropropanes to dehydrochlorination reactor 110.

For the process shown in FIG. 1, the first dehydrochlorination step, at dehydrochlorination reactor 102, occurs prior to a first chlorination step, at chlorination reactor 106 as fresh TCP is fed to reactor 102. Further, the TCP, tetrachloropropanes and other isomers are advantageously dehydrochlorinated in the same vapor phase dehydrochlorination reactor, dehydrochlorination reactor 102, and at substantially the same conditions, although the inlet composition to reactor 102 will depend on the relative reaction rates of the dehydrochlorination reactions. Generally speaking, the inlet composition will be between 30-70 mole % TCP and 30 to 70 mole % 1,2,2,3 tetrachloropropane and other tetrachloropropane isomers. If the rates are the same for both reactants, the inlet composition may be nearly the same for all reactants.

Figure 2:
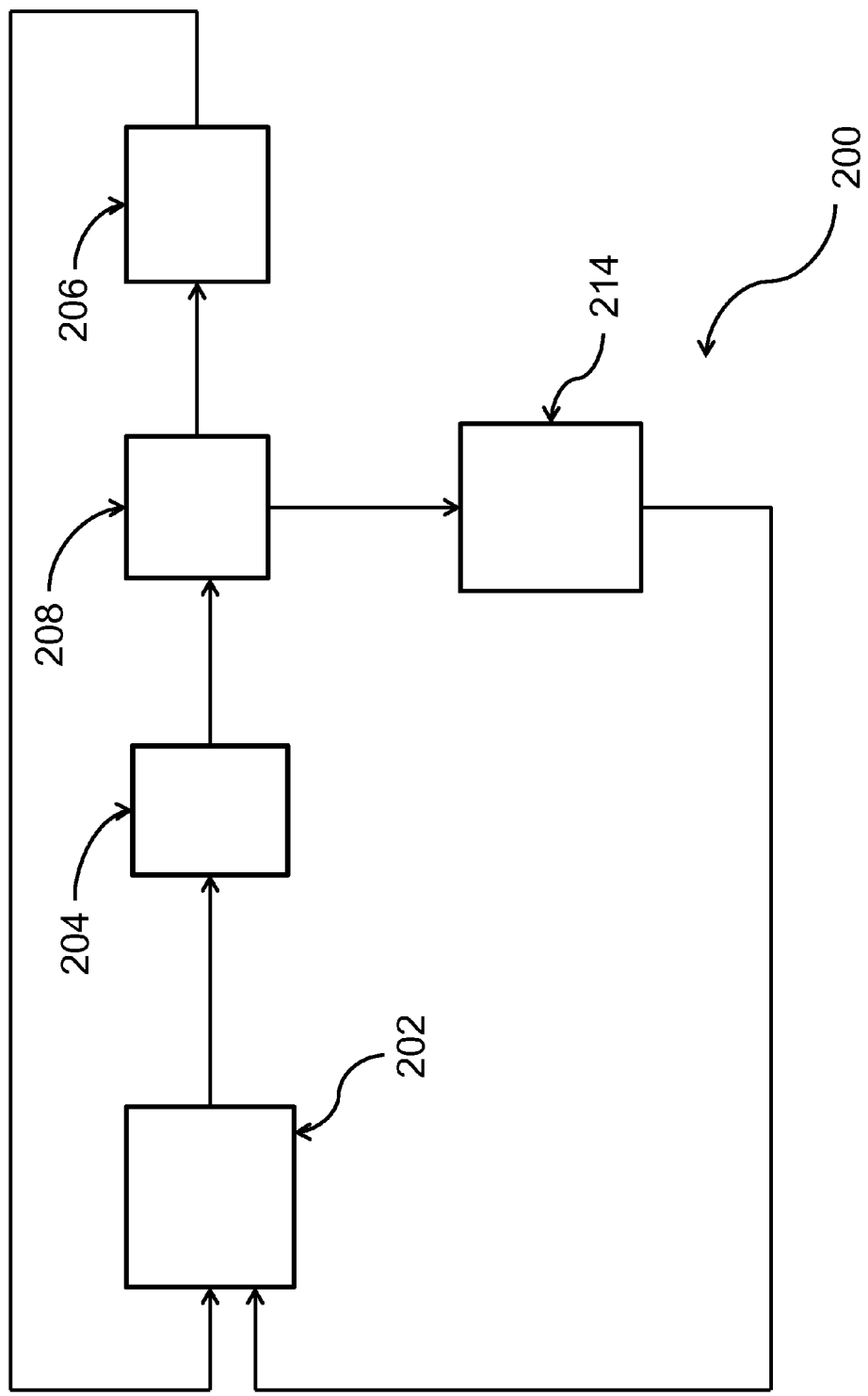
FIG. 2 is a schematic diagram of a process according to a further embodiment.

One further exemplary process for the production of chlorinated propenes is schematically illustrated in FIG. 2. Process 200 is similar to process 100, except that only one dehydrochlorination reactor is used. Process 200 makes use of dehydrochlorination reactor 202, separation columns 204, 208 and 214 and chlorination reactor 206.

In operation, fresh 1,2,3-trichloropropane is fed into vapor phase dehydrochlorination reactor 202 along with recycled 1,2,3-trichloropropane, and optionally, tetra- and pentachloropropane isomers. Dehydrochlorination reactor 202 is desirably operated at conditions sufficient to produce HCl, dichloropropenes, trichloropropenes, 1,1,2,3-TCPE and unreacted chloropropanes. After HCl is removed in separation column 204, a product stream comprising unreacted TCP is taken overhead from separation column 208 and sent to chlorination reactor 206.

The chlorinated product stream from chlorination reactor 206 is recycled back to dehydrochlorination reactor 202. The bottoms stream from separation column 208, comprising 1,1,2,3 TCPE and 2,3,3,3-TCPE, and tetra- and pentachloropropanes, is fed to separation column 214. Separation column 214 recovers 1,1,2,3-TCPE and its isomer as overhead products, recycles tetra- and pentachloropropanes to dehydrochlorination reactor 202 and purges heavier by-products. The 2,3,3,3-tetrachloropropene isomer is further converted to TCPE in an isomerization unit (not shown).

For process 200, the first dehydrochlorination step, at dehydrochlorination reactor 202, occurs prior to a first chlorination step as fresh TCP is fed to reactor 202. Further, the TCP, tetrachloropropanes, pentachloropropanes, and other isomers are advantageously dehydrochlorinated in the same vapor phase dehydrochlorination reactor, dehydrochlorination reactor 202, and at substantially the same conditions, although the inlet composition to reactor 202 will depend on the relative reaction rates of the dehydrochlorination reactions. Generally speaking, the inlet composition will be between 20-50 mole % TCP and 20-50 mole % 1,2,2,3 tetrachloropropane, and 20 to 50 mole % pentachloropropane. If the rates are the same for both reactants, the inlet composition may be nearly the same for all reactants.

Figure 3:
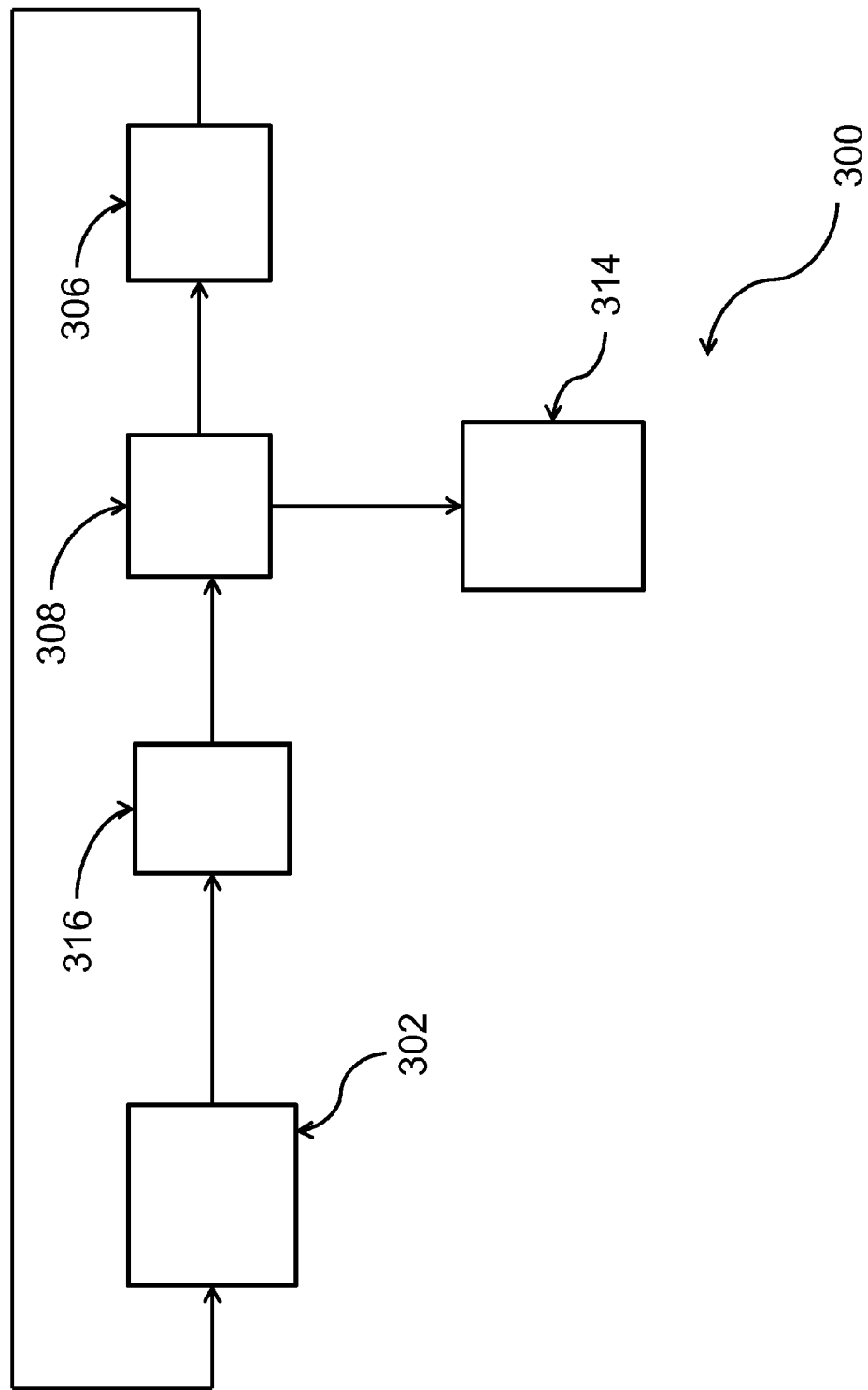
FIG. 3 is a schematic diagram of a process according to a further embodiment.

A further embodiment of the present process is shown in FIG. 3. More specifically, FIG. 3 shows process 300 where the first, and only, dehydrochlorination reactor occurs in liquid phase caustic dehydrochlorination reactor 302. Process 300 also makes use of drying column 316, chlorination reactor 306, and separation columns 308 and 314.

In operation, TCP, supplemented with tetrachloropropane and pentachloropropane isomers, is recycled from chlorination reactor 306 and fed to caustic dehydrochlorination reactor 302 together with fresh TCP. This feed stream is dehydrochlorinated within dehydrochlorination reactor 302 to 2,3-dichloropropene, 1,2,3-trichloropropene, and TCPE, and the product stream fed to drying column 316.

After drying in column 316, the overhead crude product stream, comprising di-, tri- and tetra-chloropropenes, is fed to separation column 308. The lighter olefins, i.e., the di- and trichloropropenes, are sent overhead from refining column 308 to chlorination reactor 306, and then recycled back to the dehydrochlorination reactor 302. The TCPE is recovered from separation column 308 as a bottoms stream and taken overhead from final separation column 314, while the heavier by-products are purged.

For process 300, the first dehydrochlorination step, at dehydrochlorination reactor 302, occurs prior to a first chlorination step, since fresh TCP is fed to reactor 302. And, all dehydrochlorination reactions, e.g., of TCP, tetrachloropropanes, and pentachloropropanes, etc., are carried out in liquid phase caustic dehydrochlorination reactor 302. Even though process 300 generates NaCl rather than anhydrous HCl it is simplified compared to conventional process at least because it requires less equipment. Furthermore, no vapor phase catalyst is required. As a result, catalyst life and fouling are not expected to be significant issues. Process 300 is also operable at mild operating conditions so that energy savings are provided. Process 300 is thus considered to provide benefits commensurate with the present invention and thus, to be within its scope.

The chlorinated propenes produced by the present process may typically be processed to provide further downstream products including hydrofluoroolefins, such as, for example, 1,3,3,3-tetrafluoroprop-1-ene (HFO-1234ze). Since the present invention provides an improved process for the production of chlorinated propenes, it is contemplated that the improvements provided will carry forward to provide improvements to these downstream processes and/or products. Improved methods for the production of hydrofluoroolefins, e.g., such as 2,3,3,3-tetrafluoroprop-1-ene (HFO-1234yf), are thus also provided herein.

The conversion of chlorinated propenes to provide hydrofluoroolefins may broadly comprise a single reaction or two or more reactions involving fluorination of a compound of the formula $C(X)_m CCl(Y)_n(C)(X)_m$ to at least one compound of the formula $CF_3CF=CHZ$, where each X, Y and Z is independently H, F, Cl, I or Br, and each m is independently 1, 2 or 3 and n is 0 or 1. A more specific example might involve a multi-step process wherein a feedstock of a chlorinated propene is fluorinated in a catalyzed, gas phase reaction to form a compound such as 1-chloro-3,3,3-trifluoropropene (1233zd). The 1-chloro-2,3,3,3-tetrafluoropropane is then dehydrochlorinated to 2,3,3,3-tetrafluoroprop-1-ene or 1,3,3,3-tetrafluoroprop-1-ene via a catalyzed, gas phase reaction.

EXAMPLE 1

A flask equipped with a stir bar is charged with tetrabutylammonium chloride (20 mg) and 7 g of a mixture of 1,2,3-trichloropropane and 1,2,2,3-tetrachloropropane. The mixture is flushed with nitrogen and heated to 80° C. An aqueous solution of NaOH (9 mL, 5 N) is added dropwise over several minutes. The mixture is stirred vigorously at 80° C. and sampled after 1 and 3 h. Analysis by 1H NMR spectroscopy indicates the reaction mixture compositions shown in Table 1.

TABLE 1

| | Time (min) | | |
| --- | --- | --- | --- |
| | 0 | 60 | 180 |
| Substrate | mol % | | |
| 123 trichloropropane | 71 | 10 | 2 |
| 1223 tetrachloropropane | 28 | 9 | 4 |
| 23 dichloropropene | 0 | 61 | 66 |
| 123 trichloropropene | 0 | 20 | 28 |

EXAMPLE 2

A pressure reactor is charged with a mixture of di- and trichloropropenes (3.35 g) and carbon tetrachloride (45 mL). Stirring (900 rpm) is initiated and the reactor is pressurized with a chlorine/nitrogen mixture (30% $Cl_2$ v/v) to a pressure of ~140 psig. The chlorine/nitrogen mixture is passed through the reactor at 140 psig for about 30 minutes at 25° C. and a flow rate of 200 sccm. The mixture is then sampled and analyzed by 1H NMR spectroscopy which indicated that 2,3-dichloropropene and 1,2,3-trichloropropene are converted to 1223-tetrachloropropane and 11223-pentachloroprane, respectively, with high selectivity. The results are shown in Table 2, below.

TABLE 2

| | Time (min) | |
| --- | --- | --- |
| | 0 | 30 |
| substrate | mol % | |
| 123 trichloropropane | 2 | 1 |
| 1123 tetrachloropropane | | 1 |
| 1223 tetrachloropropane | 4 | 63 |
| 11223 pentachloropropane | | 24 |
| 112233 hexachloropropane | | 1 |
| 23 dichloropropene | 66 | 5 |
| 123 trichloropropene | 28 | 5 |

The invention claimed is:
1. A continuous process for the production of chlorinated propenes from a feed comprising 1,2,3-trichloropropane, wherein a dehydrochlorination reaction occurs prior to a first chlorination reaction, at least one dehydrochlorination reaction occurs in the liquid phase, at least a portion of the product stream of the first chlorination reaction is recycled to a first dehydrochlorination reactor, at least two chlorination reac- tions or at least two dehydrochlorination reactions occur in the same reactor, and selectivity to the desired chlorinated propene is 80% or higher, and wherein the recycled product stream of the first chlorination reaction comprises at least two chloropropanes.

2. The process of claim 1, wherein at least two chlorination reactions occur in the same reactor.

3. The process of claim 1 or 2, wherein at least two dehydrochlorination reactions occur in the same reactor.

4. The process of claim 1, wherein at least one chlorination reaction is conducted in the liquid phase, and the chlorinating agent comprises $Cl_2$, $SO_2Cl_2$, or a combination of these.

5. The process of claim 4, wherein the chlorination reaction is conducted in the presence of an ionic chlorination catalyst comprising $AlCl_3$, $I_2$, $FeCl_3$, sulphur, iron, antimony pentachloride, boron trichloride, one or more lanthanum halides, one or more metal triflates, or combinations of these.

6. The process of claim 4, wherein the chlorination reaction is conducted in the presence of a free radical initiator comprising azobisisobutyronitrile, 1,1'-azobis(cyclohexanecarbonitrile), 2,2'-azobis(2,4-dimethyl valeronitrile), and dimethyl 2,2'-azobis(2-methylpropionate), or combinations of these.

7. The process of claim 1, wherein the feed further comprises allyl chloride.

8. The process of claim 1 or 7, wherein at least component of the feed stream is generated within, or upstream of, the process.

9. The process of claim 1, wherein the first dehydrochlorination reaction occurs in the vapor phase and produces a product stream comprising anhydrous HCl.

10. The process of claim 1, wherein the first dehydrochlorination reaction occurs in the liquid phase.

11. The process of claim 10, wherein the first dehydrochlorination reaction produces a mixture comprising dichloropropenes, trichloropropenes and TCPE.

12. The process of claim 1, wherein the chlorinated propene comprises 3-5 chlorine atoms.

13. The process of claim 12, wherein the chlorinated propene comprises 1,1,2,3-tetrachloropropene.

14. A process for preparing 2,3,3,3-tetrafluoroprop-1-ene or 1,3,3,3-tetrafluoroprop-1-ene comprising providing a chlorinated propene prepared by the process of claim 1 and converting the chlorinated propene into 2,3,3,3-tetrafluoroprop-1-ene or 1,3,3,3-tetrafluoroprop-1-ene.

* * * * *